United States Patent [19]
Prickett

[11] Patent Number: 5,028,423
[45] Date of Patent: Jul. 2, 1991

[54] IMMUNOGENIC CONJUGATES COMPRISING LEUKOTOXIN PEPTIDE FRAGMENTS

[75] Inventor: Kathryn S. Prickett, Seattle, Wash.

[73] Assignee: Immunex Corporation, Seattle, Wash.

[21] Appl. No.: 212,804

[22] Filed: Jun. 29, 1988

Related U.S. Application Data

[63] Continuation-in-part of Ser. No. 916,123, Oct. 7, 1986, abandoned.

[51] Int. Cl.$^5$ ............... A61K 39/385; A61K 39/395;
    A61K 39/102; A61K 39/40
[52] U.S. Cl. .................................... 424/85.8; 424/87;
    424/88; 424/92; 530/327; 530/345; 530/350;
    530/807
[58] Field of Search ............... 530/327, 345, 350, 807;
    424/85.8, 87, 88, 92

[56] References Cited

U.S. PATENT DOCUMENTS 4,474,757 10/1984 Arnon et al. ........................... 424/88
4,591,552  5/1986 Neurath ................................. 435/7

FOREIGN PATENT DOCUMENTS 0114759  8/1984  European Pat. Off. .

OTHER PUBLICATIONS

Confer, et al., "Serum Antibodies to *Pasteurella haemolytica* Lipopolysaccharide: Relationship to Experimental Bovine Pneumonic Pasteurellosis", *Am J Vet Res*, 47:1134–1138 (1986).

Gentry, et al., "Serum Neutralization of Cytotoxin from *Pasteurella Haemolytica*, Serotype 1 and Resistance to Experimental Boving Pneumonic *Pasterurellosis*", *Vet Imm & Immunopathology*, 9:239–250 (1985).

Himmel, et al., "Purification and Partial Characterization of a Macrophage Cytotoxin from Pasteurella Haemolytica", Am J Vet Res, 43:764–767 (1982).

Chang, et al., "*Pasteurella Haemolytica* Leukotoxin: Physicochemical Characteristics and Susceptibility of Leukotoxin to Enzymatic Treatment", *Am J Vet Res*, 47:716–723 (1986).

*Chem Abstracts 104:* "Cloning and Expression of the Leukotoxin Gene of Pasteurella Haemolytica A1 in Escherichia coli K-12", 16066c (1986).

Sela et al., Handbook of Experimental Immunology, vol. 1, Immunochemistry, Weir (ed.), Blackwell Scientific Publications, Boston, pp. 2.1–2.12 (1986).

Makela et al., Handbook of Experimental Immunology, vol. I, Immunochemistry, Weir (ed.), Blackwell Scientific Publications, Boston, pp. 3.1–3.13 (1986).

Rudinger, Peptide Hormones, Parsons (ed.), U. Park Press, Baltimore, pp. 1–7 (1976).

*Primary Examiner*—John Doll
*Assistant Examiner*—Christina Chan

[57] ABSTRACT

Conjugate immunogens are disclosed, comprising peptide fragments having substantial homology to the N-terminal region of *Pasteurella haemolytica* leukotoxins, covalently linked to suitable carrier proteins.

31 Claims, No Drawings

IMMUNOGENIC CONJUGATES COMPRISING LEUKOTOXIN PEPTIDE FRAGMENTS

CROSS-REFERENCE TO RELATED APPLICATION

This is a continuation-in-part of application Ser. No. 06/916,123, filed Oct. 7, 1986, now abandoned.

BACKGROUND OF THE INVENTION

The present invention relates generally to immunogenic peptide-carrier protein conjugates, and particularly to conjugates comprising selected fragments of bacterial proteins and larger carrier proteins, which are useful in providing immunity to bovine respiratory disease.

Pneumonic pasteurellosis, also known as shipping fever, is a widespread cause of mortality and morbidity of feedlot cattle in North America. Affected cattle develop a fibrinous pneumonia marked by fever, severe pulmonary inflammation, accumulation of a fibrin-laden exudate in the lungs and pleura, and necrosis of alveolar tissue. Pneumonic pasteurellosis is the central component of the multifactorial syndrome known as bovine respiratory disease (BRD), in which stress and viral infection interact to compromise normal host defenses and enable bacterial colonization of the deepest regions of the bovine lung. In North America, the annual economic losses attributable to BRD via direct deaths, weight losses, and reduced productivity have been estimated to range between $200 and $500 million.

*Pasteurella haemolytica* (*P. haemolytica*), the etiologic agent of pasteurellosis, is a normal bacterial component of the upper respiratory tract of cattle. Under normal conditions, inhaled organisms reaching the lung encounter local cellular immunity provided by resident or elicited alveolar macrophages and neutrophils. During the course of bovine respiratory disease, however, a viral infection, combined with stress attributable to handling of feedlot cattle, results in immunosuppression, allowing *P. haemolytica* bacteria to gain access and multiply in the deep regions of the lung.

Attempts to control the disease by prophylactic or therapeutic means have been largely unsuccessful. Vaccination with killed *P. haemolytica* bacterins provides no protection against pneumonic pasteurellosis in cattle, nor does such vaccination reduce lung lesions in calves challenged experimentally by intraalveolar aspiration of live *P. haemolytica*. In contrast, vaccination with live *P. haemolytica* or culture supernatants has been shown to reduce the severity of pasteurellosis lesions in challenged calves. Such results suggest that live bacteria secrete a factor capable of inducing partial immunity to the effects of pasteurellosis.

Actively growing cultures of *P. haemolytica* elaborate an exotoxin capable of killing bovine leukocytes. This cytotoxin, or leukotoxin, is optimally produced by log phase cultures and is not evident in stationary phase cultures of the bacteria. Since leukotoxin is only elaborated by living bacteria, killed bacterins prepared from washed bacteria would not contain the toxin and would not, therefore, induce protective immunity against the toxin.

Partial purification of *P. haemolytica* leukotoxin has been reported by Himmel et al., *Am. J. Vet. Res.* 43:764 (1982), and Chang et al., *Am. J. Vet. Res.* 47:716 (1986). Ultrafiltration, gel filtration and polyacrylamide gel electrophoresis have indicated leukotoxin to be a 100-150 MW protein. Leukotoxin activity is $O_2$ stable, but exquisitely heat sensitive, which has as yet precluded total purification of leukotoxin. Lacking homogeneous protein, sequencing of leukotoxin is impossible, rendering molecular manipulation at the gene level difficult.

Purification of *P. haemolytica* leukotoxin to a single protein moiety and elucidation of its amino-terminal sequence has enabled construction of immunogenic conjugates comprising leukotoxin N-terminal peptide fragments covalently joined to suitable carrier proteins. When administered to a subject animal, these conjugates are capable of eliciting antibody which specifically neutralizes the toxic effect of the *P. haemolytica* exotoxin on bovine leukocytes.

SUMMARY OF THE INVENTION

The present invention provides conjugated immunogens comprising a peptide fragment having substantially homology to the N-terminal region of a *Pasteurella haemolytica* leukotoxin, covalently linked to a carrier protein. In related aspects, the invention provides immunogenic compositions comprising such conjugated immunogens, and methods of inducing anti-leukotoxin antibody production in a mammal, comprising administering immunogenically effective amounts of the compositions.

DETAILED DESCRIPTION OF THE INVENTION

Substances having molecular weights less than 1000 daltons are not ordinarily antigenic. However, antibodies can be raised to small molecules by immunization with conjugates consisting of low molecular weight substances (haptens) covalently linked to proteins or synthetic polypeptides.

The immunogens of this invention are antigenic hapten-carrier conjugates comprising a peptide of 5-20 amino acids covalently joined to a suitable carrier protein. The peptide, or hapten, component of the conjugates of the invention is characterized by substantial homology to all or part of one of the following N-terminal peptide sequences of *P. haemolytica* leukotoxin type 10 and type 1, designated respectively as LeukoT-1 and LeukoT-2:

Gly-Asn-Lys-Phe-Thr-Asn-Ile-Ser-Thr-Asn-Leu-Arg and

Gly-Thr-Arg-Leu-Thr-Thr-Leu-Ser-Asn-Gly-Leu-Lys.

Purified *P. haemolytica* leukotoxin type 10 was sequenced as detailed below.

In a preferred aspect, a conjugate immunogen according to the present invention comprises a peptide selected from the group consisting of Gly-Asn-Lys-Phe-Thr-Asn-Ile-Ser-Thr-Asn-Leu-Arg-X, and Gly-Thr-Arg-Leu-Thr-Thr-Leu-Ser-Asn-Gly-Leu-Lys-X covalently linked via moiety X to a carrier protein, wherein X is $(A^1-A^n)$, where $A^1$ through $A^n$ are the same or different and can be any amino acid or a derivative thereof, and n is an integer from 1-10. In this context, "derivative" means an amino acid modified by covalent attachment of a crosslinking group.

"Substantial homology," as used throughout the specification, means that a subject amino acid sequence, for example, a peptide fragment, varies from a reference sequence by one or more substitutions, deletions, or additions, the net effect of which do not result in a significant antigenic dissimilarity between the reference and subject sequences. Antigenic similarity is measured by cross-reactivity of antibody, raised in response to immunization with a conjugate comprising the subject sequence, with an antigenic determinant provided by the reference sequence.

It will be apparent to those skilled in the art that analog peptides, varying from the foregoing sequence by one or more amino acid deletions, insertions, or conservative substitutions, could be synthesized. Substitutions of this type include Ser or Thr for Gly; His or Asp for Asn; Arg for Lys; Tyr for Phe; Ser or Gly for Thr; Val or Leu for Ile; Val, Ile, or Met for Leu; and His or Lys for Arg. Similarly, peptides of somewhat greater or lesser size could be prepared. Depending upon the extent of such changes, such analogs may well be antigenically similar or indistinguishable when compared to the foregoing sequence. Conjugate immunogens comprising such analog peptides are thus considered obvious equivalents of the immunogens disclosed and claimed herein.

Suitable carrier proteins include globulin fractions, the serum albumins of various species, hemocyanin, ovalbumin, lactalbumin, thyroglobulin, and fibrinogen. Soluble or insoluble conjugates can be employed in immunization, although soluble conjugates are preferred. In addition, synthetic polypeptides, for example poly(L-lysine), can be employed as carriers. However, proteins such as ovalbumin and bovine serum albumin are preferred for use in preparing the conjugates of the present invention.

The number of haptens bound to the carrier protein can vary from 2 to 50, depending upon the conditions of conjugation. Preferably, a given carrier has, on average, at least five peptide haptens covalently attached. Generally, higher antibody titers are obtained using conjugates having higher epitope densities.

The spacer group linking peptide to carrier, designated X in the foregoing formula, will generally comprise one or more amino acids, one of which provides a free sulfhydryl, carboxyl, amino or other group for conjugation to the protein carrier. The method of conjugation should be selected so as to avoid unwanted structural alteration of the hapten, and so that the crosslinking group is not bound to the antigenically distinctive part of the hapten molecule. For this reason, the group selected for conjugation should not be present in the peptide hapten sequence itself, or should be blocked if present, to avoid conjugation at locations other than the preferred crosslinking site at or near the C-terminal of the peptide. Exemplary coupling methods are summarized in the following paragraphs.

The C terminal of the peptide, or of an aspartic or glutamic acid residue added to the peptide, provides a carboxyl group that can be conjugated to an amino group of a carrier protein using a mixed anhydride procedure. In this reaction, a haptenic carboxyl group is converted to an acid anhydride, which is then coupled to a free amino group of the carrier in an aqueous acetone solution. Suitable mixed anhydride procedures are disclosed by Vaughn et al., *J. Am. Chem. Soc.* 74:676 (1952), and Karol et al., *Proc. Natl. Acad. Sci. U.S.A.* 57:713 (1967).

An alternative conjugation procedure employing haptenic carboxyl groups employs carbodiimide reagents, for example, 1-ethyl-3(3-dimethylaminopropyl)-carbodiimide-HCl, (EDAC), 1-cyclohexyl-3-[2-morpholinyl-(4)ethyl]carbodiimide, or methyl-p-toluenesulfate. When these reagents are employed, the amino terminal of the peptide should be blocked by an appropriate reagent, for example, a tert-butyloxycarbonyl (BOC) group. Carbodiimides can also be used to couple free amino groups of the hapten to free carboxyl groups of the carrier. References disclosing suitable procedures useful in conjugating peptides to proteins by carbodiimide methods include Bauminger et al., *Methods in Enzymology* 70:151 (1980); Goodfriend et al., *Science* 143:1344 (1964), and Jaffe et al., *Immunochemistry* 7:715 (1970). Carbodiimide coupling reagents are commercially available (Biorad Laboratories, Richmond, Calif., U.S.A.) and product literature discloses applicable techniques for use.

Peptides can be coupled to carrier proteins by conversion of haptenic amino groups to p-nitrobenzolyamide by reaction with p-nitrobenzyl chloride. The amide derivative is then reduced to a p-aminobenzoyl derivative which can be coupled to proteins by diazotization. References disclosing such conjugations include Anderer, *Biochim. Biophys. Acta* 71:246 (1963) and Deodhar, *J. Exp. Med.* 111:419, 429 (1960). Alternatively, amino-amino conjugations can be effected using glutaraldehyde as a coupling reagent, for example, as disclosed by Reichlin, *Methods in Enzymology* 70:159 (1980). When an amino coupling strategy is adopted, the terminal amino group of the peptide should first be blocked to prevent conjugation at the N-terminus.

A convenient and preferred conjugation strategy relies upon formation of a bond between a cysteine residue in the coupling region of the hapten and amino groups in the carrier protein. A suitable procedure employs m-maleimidobenzoyl-N-hydroxy succinimide ester (MBS). This reagent can be reacted with free amino groups on the carrier protein, to provide an MBS-acylated intermediate which is then reacted with the free thiol group of the peptide to provide a conjugate. A suitable technique for use of MBS is disclosed by Kitagawa et al., *J. Biochem.* 94:1165 (1983).

Following conjugation, unreacted materials are separated from the conjugated immunogen by extensive dialysis or gel filtration.

To administer the conjugates to cattle, compositions can be prepared which comprise a physiologically acceptable carrier or diluent, for example phosphate-buffered saline. To potentiate the antibody response to immunization, such compositions can optionally comprise an adjuvant such as mineral oil or aluminum hydroxide. Immunization is preferably conducted by intramuscular injection of an initial dose of immunogen followed several weeks later by a booster. An initial inoculation can consist of from 0.1–10 mg of conjugate, followed by a booster of approximately half the initial dose.

The following examples illustrate particular aspects of the present invention.

EXAMPLE 1: PURIFICATION OF LEUKOTOXIN TYPE 10

A. Culture of *P. haemolytica*

*P. haemolytica* serotype 10 was obtained from the American Type Culture Collection (ATCC No. 29706) in a lyophilized form. After reconstitution, a large culture was grown in nutrient medium overnight and subsequently frozen in 1 ml aliquots at −80° C. These aliquots were used as seed inocula for preparation of leukotoxin.

Following experiments designed to determine optimum conditions for leukotoxin elaboration, a series of shake-flask cultures were conducted and the supernatants collected as follows. Bacteria, taken from log-phase growth, were seeded in 250 ml Erlenmyer flasks containing 75 ml LB broth, and incubated for 4–5 hr at 37° C. on an orbital shaker at 250 cycles/min. All subsequent steps were performed at 4° C. Bacteria were removed by centrifugation (3000× g, 20 min.), 250 μm EDTA was added, and supernatant fluid was filtered through a 0.8 μm filter. As a positive control for use in assays of leukotoxin activity, an early preparation of roughly 200 ml was dispersed in 1 ml aliquots and stored at −80° C.

Concentrated crude leukotoxin was prepared by subjecting the foregoing filtered supernatants to ultrafiltration, using a hollow fiber cartridge having a 10,000 dalton molecular weight cutoff (Amicon Corporation, Danvers, Mass., U.S.A.).

B. Leukotoxin Assay

Leukotoxin activity was assayed by the ability to kill the bovine T cell line, BL3. Briefly, BL3 cells were labeled at 37° C. for 1 hr with 250 μCi $^{51}$Cr (New England Nuclear, Boston, Mass., U.S.A.), washed twice through fetal calf serum (FCS), and adjusted in RPMI 1640 medium containing 10% FCS to a cell density of $5 \times 10^5$/ml.

Samples to be assayed were diluted (100 μl, log$_2$) across eight or 12 wells of 96 well round bottom microtiter plates (Linbro, McLean, Va., U.S.A.). Four to six wells in each assay contained either 100 μl medium or 100 μl of a lysing reagent (6 drops per 10 ml water of a solution containing 115 g/l cationic surfactant, 3.0 g/l KCN, and 0.1 g/l potassium ferricyanide, available from American Scientific Products, McGraw Park, Ill., U.S.A.). Wells containing medium only served as a negative control, and those containing the lysing reagent served as a maximum lysis control. Radiolabeled BL3 cells (100 μl) were then added to each well and plates were incubated at 37° C. for 1 hr. Thereafter, plates were centrifuged at 300× g for 10 min at 4° C. Medium (100 μl) was removed from the top of each well, and placed into 3.5 ml Ecoscint scintillation fluid (National Diagnostics, Somerville, N.J., U.S.A.) in minivials. These were assessed for decay (counts per minute, cpm) using a Packard Minaxi Tri-Carb 4000 Series liquid scintillation counter with windows set as for tritium. Percent cytolysis of BL3 targets was calculated as follows:

$$\frac{\text{Sample cpm} - \text{Mean Medium cpm}}{\text{Mean Maximum cpm} - \text{Mean Medium cpm}} \times 100$$

To quantify sample values for comparison purposes, frozen crude leukotoxin standard was assigned a value of 1 unit/ml leukotoxin activity and all samples were evaluated against it by relating the inverse dilution (log$_2$) which gave 50% cytolysis to that of the standard providing similar cell killing.

C. Purification

Leukotoxin, concentrated by ultrafiltration, was applied to a 1.6 cm ×30 cm column of DEAE-Sephacel (Pharmacia Fine Chemicals, Piscataway, N.J., U.S.A.) or QAE-Sepharose (diethyl-[2-hydroxypropyl]aminoethyl-agarose conjugate, fast flow, Pharmacia Fine Chemicals) previously equilibrated with 50 mM Tris/250 μM EDTA/85 mM NaCl, pH 7.4 (TEN) buffer at 20 ml/hr at 4° C. Columns were washed with 3 column volumes of starting buffer, and then eluted in a linear gradient (3 column volumes) ranging from 85 mM to 500 mM NaCl in 50 nM Tris/250 μM EDTA, pH 7.4. Fractions of 5 ml were collected, assayed for leukotoxin activity against BL3 targets, and measured for osmolarity. Leukotoxin eluted from both anion exchange media at 200 mM NaCl. Fractions containing peak activity were pooled, divided into aliquots, and frozen at −80° C. for future use.

SDS-PAGE was performed on the active leukotoxin fractions, non-active side fractions, and pooled active fractions derived from DEAE ion exchange chromatography in order to visualize those proteins of MW 100,000 or greater. In this procedure, a discontinuous Tris-glycine system substantially similar to that disclosed by Laemmli, Nature 277:680 (1970) was employed, and molecular weight was determined using the following protein standards: thyroglobulin (669,000), ferritin (440,000), catalase (232,000), lactate dehydrogenase (140,000), and bovine serum albumin (67,000).

Silver staining revealed only one protein in the active fractions which was larger than 100 kilodaltons. Similar fractions from LB broth controls eluted from DEAE-Sephacel had no bands of comparable size on gels.

Peak leukotoxin-containing fractions from anion exchange chromatography were pooled and reduced by vacuum evaporation to about 1 ml. A fraction (200 μl) of this material was applied to a 1 cm ×25 cm column containing Sephacryl S-200 (Pharmacia) equilibrated at 10 ml/hr with phosphate buffered saline containing 250 μM EDTA. Fractions of 0.5 ml were collected, monitored for protein by absorbance at 280 nm, and assayed for leukotoxin activity as described above.

Fractions eluting from the S-200 gel which displayed leukotoxin activity were electrophoresed and stained with silver nitrate. A 110 kilodalton band was prominent in the active fractions; however, other minor bands were still visible.

Since consecutive anion exchange and gel exclusion chromatography procedures did not yield a homogeneous 110,000 dalton protein, electroelution of leukotoxin from pooled ion exchange chromatography fractions was performed. Partially purified leukotoxin from anion exchange chromatography was dialyzed against 10 mM NH$_4$HCO$_3$ containing 0.02% (v/v) SDS. Following dialysis, the material was concentrated to 50 μl in vacuo and then applied to a 5–20% acrylamide gradient Laemmli gel (0.75 mm thickness). Subsequent staining, excision and electroelution were performed as described by Hunkapiller et al., Meth. Enzymol. 91:227 (1983).

Electroelution of protein from the 110 kilodalton band yielded material with specific leukotoxin activity. SDS-polyacrylamide gel electrophoresis of electroeluted leukotoxin revealed only a 110 kd band after silver staining.

D. Protein Sequencing

Amino-terminal protein sequencing was performed on 6 μg (43 pmol) of electroeluted leukotoxin as described by March et al. Nature 315:641 (1985). The sequence obtained is set forth below:
Cycle No.: 1 2 3 4 5 6 7 8 9 10 11 12 13

Amino Acid: Gly-Asn-Lys-Phe-Thr-Asn-Ile-Ser-Thr-Asn-Leu-Arg-Asn

The absolute yield of amino terminal glycine was 11.8 pmol. No other sequences were detected.

EXAMPLE 2: SYNTHESIS AND CONJUGATION OF LEUKOT-1

A synthetic peptide, corresponding to the first 12 amino acids found at the amino terminus of purified leukotoxin, and having three additional amino acids (-Gly-Cys-Gly) added to the carboxy terminus of the peptide to facilitate conjugation, was synthesized on a peptide synthesizer (Applied Biosystems, Model 430A Peptide Synthesizer) using the Merrifield solid phase method described with N-alpha-tert-butyloxy carbonyl protected amino acids, standard side chain protection and p-methylbenzhydralamine resin. After cleavage from the resin with hydrofluoric acid, free peptide was purified by high performance liquid chromatography (HPLC) on a $C_{18}$ Vydac column (1×25 cm), equilibrated in 0.1% trifluoroacetic acid (TFA), and eluted with a gradient of acetonitrile containing 0.1% TFA. The composition of the eluted peptide was confirmed by amino acid analysis. This peptide is referred to as LeukoT-1.

Dialyzed ovalbumin (OVA, Sigma Chemicals, St. Louis, Mo., U.S.A.) in 0.1M Na phosphate buffer, pH 7.0, was activated with m-maleimidobenzoyl-N-hydroxy succinimide ester and then conjugated to the peptide through its carboxy terminal sulfhydryl group, substantially as described by Liu et al., *Biochemistry* 18:690 (1979). Conjugation proceeded for 3 hrs at which time the conjugated peptide was extensively dialyzed. The coupling efficiency, determined by amino acid analysis, was approximately 3-5 peptides per molecule of OVA. The conjugate of LeukoT-1 to ovalbumin is referred to as OVA-LeukoT-1.

EXAMPLE 3: GENERATION OF ANTI-OVA-LEUKOT-1 ANTIBODY

BALB/c mice were immunized in the footpad with 25 µg of the OVA-peptide conjugate, OVA-LeukoT-1, emulsified in complete Freund's adjuvant. The animals were reimmunized three weeks later. One week following reimmunization, serum antibody titers were found to be greater than 1:22,000, as determined by enzyme-linked immunosorbant assays (ELISA).

Antibody thus generated was used in a Western blot procedure wherein leukotoxin, partially purified by ion exchange chromatography on QAE-Sepharose, served as the electrophoresed protein. Mouse anti-leukotoxin peptide/OVA was reacted with the blot, prior to addition of peroxidase-labeled anti-mouse Ig and peroxidase substrate.

In this procedure, leukotoxin, partially purified by anion exchange column chromatography, was heated in Laemmli sample buffer for 5 min and analyzed by SDS/PAGE in a 8-20% gradient gel under non-reducing conditions. Electrophoresed proteins on the gel were then electrophoretically transferred to a sheet of nitrocellulose. After transfer, the nitrocellulose was treated for 1 hr with 5% nonfat dry milk (NDM) in 50 mM Tris HCl, 150 mM NaCl, pH 7.5 (TBS) to block nonspecific binding sites. The sheet was then washed with TBS, cut into appropriate strips and incubated for 1 hr with a 1:100 dilution of normal mouse serum (NMS) or anti-OVA-LeukoT-1 mouse serum in 5% NDM/TBS. Nitrocellulose strips were again washed with TBS and incubated with horseradish peroxidase conjugated goat anti-mouse IgG (Biorad Laboratories, Richmond, Calif., U.S.A.), diluted 1:2000 in 5% NDM/TBS for 1 hr, followed by washing with TBS and incubating with substrate (4-chloro-1-napthol) for 15 min.

The only band recognized by the mouse anti-OVA-peptide antibody was the 110 kd protein.

To demonstrate neutralization of the cytotoxic effect of leukotoxin by this antibody, leukotoxin (25 µl), partially purified by ion exchange column chromatography on QAE-Sepharose, was reacted with either anti-OVA-LeukoT-1 antibody (25 µl), normal mouse serum (25 µl) or medium (25 µl) for 1 hr at room temperature with gentle rocking. Thereafter, an additional 150 µl of medium was added to each reaction mixture. Serial two-fold dilutions were then prepared and assessed for leukotoxin activity against $^{51}$Cr-labeled BL3 cells.

The anti-peptide antisera significantly neutralized the cytotoxic effect of leukotoxin, whereas neither normal serum nor medium had any neutralizing capacity.

EXAMPLE 4: SYNTHESIS AND CONJUGATION OF LEUKOT-2

A synthetic peptide corresponding to the N-terminus peptide sequence Gly-Thr-Arg-Leu-Thr-Thr-Leu-Ser-Asn-Gly-Leu-Lys of leukotoxin Type 1, amino acids 1-12, plus an additional -Gly-Cys-Gly added to the peptide's C-terminus, was synthesized on a peptide synthesizer in a manner substantially similar to that described in Example 2. This peptide is referred to as LeukoT-2.

LeukoT-2 was coupled to ovalbumin in a manner substantially as described in Example 2. The conjugate is referred to as OVA-LeukoT-2.

EXAMPLE 5: GENERATION OF ANTI-PEPTIDE ANTIBODY

Rabbits were immunized with 250 to 500 µg of the OVA-LeukoT-2 conjugate by multiple subcutaneous injections substantially as described in Example 3. Similarly, BALB/c mice were immunized with 25 µg of the OVA-LeukoT-2 conjugate.

Antibody thus generated was purified in a manner substantially similar to that described in Example 3.

To demonstrate the neutralization of the cytotoxic effect of leukotoxin by this antibody, leukotoxin was reacted with either anti-OVA-LeukoT-2 antibody, normal mouse serum, or medium for 1 hr at room temperature with gentle rocking. Thereafter, additional medium was added to each reaction mixture. Serial two-fold dilutions were then prepared and assessed for leukotoxin activity against $^{51}$Cr-labeled BL3 cells.

The anti-OVA-LeukoT-2 antisera significantly neutralized the cytotoxic effect of leukotoxin, whereas neither normal serum nor medium had any neutralizing capacity.

What is claimed is:

1. A conjugate immunogen comprising a peptide selected from the group consisting of
   Gly-Asn-Lys-Phe-Thr-Asn-Ile-Ser-Thr-Asn-Leu-Arg and
   Gly-Thr-Arg-Leu-Thr-Thr-Leu-Ser-Asn-Gly-Leu-Lys
covalently linked to a carrier protein.

2. The conjugate immunogen of claim 1, wherein the peptide is Gly-Asn-Lys-Phe-Thr-Asn-Ile-Ser-Thr-Asn-Leu-Arg [-X].

3. A conjugate immunogen according to claim 2, wherein the peptide is covalently linked via a linker moiety which comprises at least one Cys residue.

4. A conjugate immunogen according to claim 3, wherein the linker moiety is Gly-Cys-Gly.

5. A conjugate immunogen according to claim 2, wherein the carrier protein is selected from the group consisting of ovalbumin, serum albumins, hemocyanin, thyroglobulin, and fibrinogen.

6. A conjugate immunogen according to claim 5, wherein the carrier protein is ovalbumin.

7. An immunogenic composition for inducing anti-leukotoin antibody production in a mammal, comprising an immunologically acceptable amount of a conjugate immunogen according to claim 2 and an inert and physiologically acceptable carrier or diluent.

8. An immunogenic composition for inducing anti-leukotoin antibody production in a mammal, comprising an immunogenically effective amount of a conjugate immunogen according to claim 3 and an inert and physiologically acceptable carrier or diluent.

9. An immunogenic composition for inducing anti-leukotoin antibody production in a mammal, comprising an immunogenically effective amount of a conjugate immunogen according to claim 4 and an inert and physiologically acceptable carrier or diluent.

10. An immunogenic composition for inducing anti-leukotoin antibody production in a mammal, comprising an immunogenically effective amount of a conjugate immunogen according to claim 5 and an inert and physiologically acceptable carrier or diluent.

11. An immunogenic composition for inducing anti-leukotoin antibody production in a mammal, comprising an immunogenically effective amount of a conjugate immunogen according to claim 6 and an inert and physiologically acceptable carrier or diluent.

12. A method of inducing anti-leukotoxin antibody production in a mammal, comprising administering an immunogenically effective amount of a composition according to claim 7.

13. A method of inducing anti-leukotoxin antibody production in a mammal, comprising administering an immunogenically effective amount of a composition according to claim 8.

14. A method of inducing anti-leukotoxin antibody production in a mammal, comprising administering an immunogenically effective amount of a composition according to claim 9.

15. A method of inducing anti-leukotoxin antibody production in a mammal, comprising administering an immunogenically effective amount of a composition according to claim 10.

16. A method of inducing anti-leukotoxin antibody production in a mammal, comprising administering an immunogenically effective amount of a composition according to claim 11.

17. A conjugate immunogen of claim 1, wherein the peptide is Gly-Thr-Arg-Leu-Thr-Thr-Leu-Ser-Asn-Gly-Leu-Lys.

18. A conjugate immunogen according to claim 17, wherein the peptide is covalently linked via a linker moiety which comprises at least one Cys residue.

19. A conjugate immunogen according to claim 18, wherein the linker moiety if Gly-Cys-Gly.

20. A conjugate immunogen according to claim 17, wherein the carrier protein is selected from the group consisting of ovalbumin, serum albumins, hemocyanin, thyroglobulin, and fibrinogen.

21. A conjugate immunogen according to claim 20, wherein the carrier protein is ovalbumin.

22. An immunogenic composition for inducing anti-leukotoin antibody production in a mammal, comprising an immunologically acceptable amount of a conjugate immunogen according to claim 17 and an inert and physiologically acceptable carrier or diluent.

23. An immunogenic composition for inducing anti-leukotoin antibody production in a mammal, comprising an immunogenically effective amount of a conjugate immunogen according to claim 18 and an inert and physiologically acceptable carrier or diluent.

24. An immunogenic composition for inducing anti-leukotoin antibody production in a mammal, comprising an immunogenically effective amount of a conjugate immunogen according to claim 19 and an inert and physiologically acceptable carrier or diluent.

25. An immunogenic composition for inducing anti-leukotoin antibody production in a mammal, comprising an immunogenically effective amount of a conjugate immunogen according to claim 20 and an inert and physiologically acceptable carrier or diluent.

26. An immunogenic composition for inducing anti-leukotoin antibody production in a mammal, comprising an immunogenically effective amount of a conjugate immunogen according to claim 21 and an inert and physiologically acceptable carrier or diluent.

27. A method of inducing anti-leukotoxin antibody production in a mammal, comprising administering an immunogenically effective amount of a composition according to claim 22.

28. A method of inducing anti-leukotoxin antibody production in a mammal, comprising administering an immunogenically effective amount of a composition according to claim 23.

29. A method of inducing anti-leukotoxin antibody production in a mammal, comprising administering an immunogenically effective amount of a composition according to claim 24.

30. A method of inducing anti-leukotoxin antibody production in a mammal, comprising administering an immunogenically effective amount of a composition according to claim 25.

31. A method of inducing anti-leukotoxin antibody production in a mammal, comprising administering an immunogenically effective amount of a composition according to claim 26.

* * * * *

UNITED STATES PATENT AND TRADEMARK OFFICE
CERTIFICATE OF CORRECTION

PATENT NO. : 5,028,423
DATED : July 2, 1991
INVENTOR(S) : Kathryn S. Prickett

It is certified that error appears in the above-identified patent and that said Letters Patent is hereby corrected as shown below:

Column 9:
In Claim 7, line 13, "leukotoin" should be -- leukotoxin --.
In Claim 8, line 18, "leukotoin" should be -- leukotoxin --.
In Claim 9, line 23, "leukotoin" should be -- leukotoxin --.
In Claim 10, line 28, "leukotoin" should be -- leukotoxin --.
In Claim 11, line 33, "leukotoin" should be -- leukotoxin --.

Column 10:
In Claim 22, line 16, "leukotoin" should be -- leukotoxin --.
In Claim 23, line 21, "leukotoin" should be -- leukotoxin --.
In Claim 24, line 26, "leukotoin" should be -- leukotoxin --.
In Claim 25, line 31, "leukotoin" should be -- leukotoxin --.
In Claim 26, line 36, "leukotoin" should be -- leukotoxin --.

Signed and Sealed this

Fifteenth Day of December, 1992

*Attest:*

DOUGLAS B. COMER

*Attesting Officer*         *Acting Commissioner of Patents and Trademarks*